United States Patent [19]

Chapman et al.

[11] Patent Number: 4,689,386

[45] Date of Patent: Aug. 25, 1987

[54] BIOCOMPATIBLE SURFACES

[75] Inventors: Dennis Chapman, Beaconsfield, England; Gregorio P. Valencia, Barcelona, Spain

[73] Assignee: Biocompatibles Ltd., London, England

[21] Appl. No.: 893,541

[22] PCT Filed: Nov. 7, 1985

[86] PCT No.: PCT/GB85/00507

§ 371 Date: Aug. 7, 1986

§ 102(e) Date: Aug. 7, 1986

[87] PCT Pub. No.: WO86/02933

PCT Pub. Date: May 22, 1986

[30] Foreign Application Priority Data

Nov. 7, 1984 [GB] United Kingdom ............. 8428109

[51] Int. Cl.[4] ............................................ C08G 18/38
[52] U.S. Cl. .................................... 528/71; 264/328.1; 264/328.6; 264/328.8; 427/385.5
[58] Field of Search ............ 528/71; 264/328.1, 328.6, 264/328.8; 427/385.5

[56] References Cited

U.S. PATENT DOCUMENTS 3,268,360  8/1966  Beninate et al. ............... 528/71
3,498,969  3/1970  Lewis ............................. 260/211

Primary Examiner—Maurice J. Welsh
Attorney, Agent, or Firm—Nixon & Vanderhye

[57] ABSTRACT

A polyurethane reaction product of a di- or polyisocyanate and a diol or polyol having at least two hydroxyl groups capable of reacting with an isocyanate group and having the residue of at least one further hydroxyl group present in the form of a phosphorus acid ester group of formula (I), wherein n is 0 or 1, m is 2, 3, or 4 and each R independently is an alkyl group of 1 to 4 carbons optionally with a diol or polyol which does not contain a group of formula I is useful in biocompatible, particularly haemocompatible devices for use in methods of medical treatment.

16 Claims, No Drawings

BIOCOMPATIBLE SURFACES

This invention relates to biocompatible particularly haemocompatible surfaces and to new polymers based on phosphatidylcholine. Blood contacting prostheses are of major importance today in cardiovascular surgery and other fields of medicine. Heart valves and blood vessel prostheses, balloon pumps and catheters are being implanted in daily surgical practice to restore or diagnose cardiovascular function.

Artificial organs are routinely employed in blood detoxification by absorptive haemoperfusion and in oxygenation (membrane oxygenators and heart-lung devices). Considerable effort and capital is invested in Europe and the U.S.A. in the development and experimental evolution of an implantable artificial heart system. The devices are generally constructed from polymeric materials and when in use, a blood-polymer contact is present. This contact can cause a reaction in the recirculating blood, which, depending on the choice of material, the design parameter, the flow or the addition of the anticoagulants, may lead to protein deposition, adhesion and destruction of red blood cells (haemolysis), platelet (thrombocyte) adhesion and aggregation and blood coagulation leading to the formation of a haemostatic plug (thrombus). The occurrence of thromboembolism in cardiovascular surgery continues to be a problem, notwithstanding routine treatment with anticoagulants. For these reasons the search for biocompatible non-thrombogenic materials has been an important research objective over the last two decades. Our approach to this problem is to mimic the surface characteristics of cell membranes.

Biological membranes are important in all areas of the body. Every cell has an outer membrane and within the cell there are membranes that act to compartmentalise the various organelles, e.g. the mitochondria, nucleus and endoplasmic reticulum. Membranes are particularly important features of the functions of blood cells, e.g. erthrocytes and leucocytes. The various cell membranes, including those of red blood cells, are all built upon an asymmetric lipid matrix of polar lipids in which the intrinsic proteins are distributed. the outer surface of the lipid matrix of cells contains the grouping:

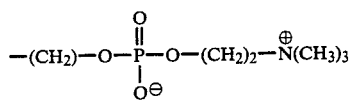

The outer polar surface is a common feature of red cells, platelets, lymphocytes, etc. The inner surface is different and usually contains the negatively charged lipids. Studies of cell systems have shown that the lipids which occur on the inner cell surface are pro-coagulant whilst those on the outer surface are thromboresistant (Zwaal, R. F. A. Comfurius, P. and van Deenen, L. M. M., Membrane asymmetry and blood coagulation, Nature, 1977, 268, 358–360).

The present invention provides a series of new polymers based upon reactions of polyols partially esterified by phosphatidylcholine or homologues thereof, isocyanates and optionally various diols or polyols, the latter having the effect of modulating the rheological characteristics of the resulting polymer. These new polymers mimic the thromboresistant surfaces of blood cell membranes and also have low antigenic character. The polymers of the invention range in rheological characteristics from soft to hard polymers and have useful applications to a variety of situations where biocompatibility particularly haemocompatibility are required ranging from new soft contact lens materials to polymers suitable for heart valves and other prosthetic devices.

The present invention provides a polyurethane reaction product of an aliphatic or aromatic di- or polyisocyanate and a diol or polyol having at least two hydroxyl groups capable of reacting with an isocyanate group and having the residue of at least one further hydroxyl group present in the form of a phosphorus acid ester of formula I:

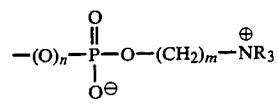

wherein n is 0 or 1, m is 2, 3 or 4 and each R independently is an alkyl group containing 1 to 4 carbon atoms.

The polymers of the present invention comprise essentially a polymer backbone having a polyurethane structure carrying pendant groups containing the phosphatidylcholine residue or homologue thereof. The exact nature of the backbone and the proportion and disposition of the phosphatidylcholine or homologue thereof side chains is controlled by the nature and proportions of the starting materials and this, in turn, will be influenced by the intended use of the polymers since, as will be explained in more detail below, it is possible to produce the polymers of the invention in various physical forms.

The primary reagents used in this invention are the diol or polyol component and the isocyanate component. It is necessary that the diol or polyol component has at least two hydroxyl groups available for reaction with the isocyanate to form the polyurethane structure. If more than two such hydroxyl groups are available in the polyol component, then the resulting polyurethane can have a crosslinked structure although crosslinking can, of course, also be introduced by the use of polyfunctional isocyanates by which we mean isocyanates containing at least three reactive isocyanate groups in the molecule.

The basic reaction for producing the present range of new polyurethanes is to link e.g. glycerophosphatidyl choline with a suitable diisocyanate. The urethane group results from the interaction of an isocyanate and a hydroxy compound as follows:

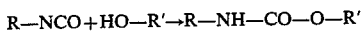

When multifunctional reactants are used this reaction leads to polyurethanes, in other words, when a diisocyanate and a diol react together a linear polyurethane is obtained.

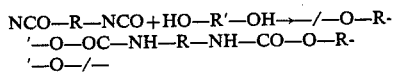

On the other hand when a diisocyanate and a polyol are used a crosslinked polymer is obtained. A crosslinked polyurethane can also be derived from an isocyanate with more than two active groups and a diol. Modulation of the rheological properties of these polymers may be achieved by using a second diol or polyol along with the basic glycerophosphatidyl derivative. In this way the two hydroxyl components can copolymerise with the diisocyanate to give a polyurethane-type polymer.

There is a wide range of diols and polyols available which do not contain a group of formula I and naming as R″ the main organic skeleton of such components we can say that those compounds will contribute to the main polymer structure in the following way:

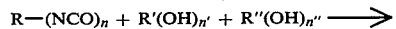

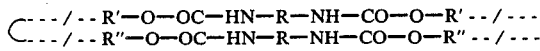

Some examples of those R″ structures are:

| | |
|---|---|
| Ethylene glycol | OH—CH₂—CH₂—OH |
| Propylene glycol | OH—CH₂—CH₂—CH₂—OH |
| 1,2-Propylene glycol | 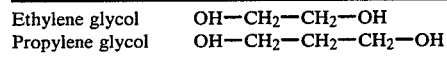 |
| 1,4-Butanediol | OH—CH₂—CH₂—CH₂—CH₂—OH |
| 1,3-Butanediol | 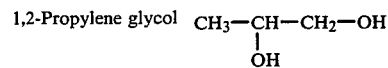 |
| 1,5-Pentanediol | OH—CH₂—CH₂—CH₂—CH₂—CH₂—OH |
| Glycerol | 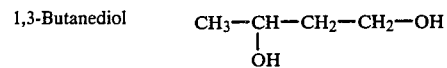 |
| Trimethylolpropane | CH₃—CH₂—C(CH₂—OH)₃ |

The raw material used to provide the urethane bond with the hydroxyl groups is the isocyanate. Since we are interested in using a multifunctional reactant different possibilities arise, and the isocyanate may be e.g.

TDI Tolylenediisocyanate
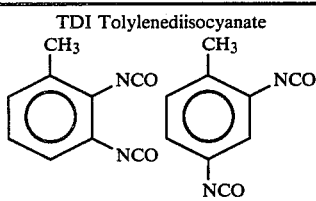

MDI Diphenylmethane diisocyanate
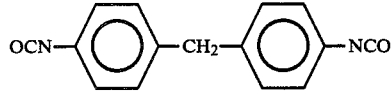

NDI Naphthylene 1,5-diisocyanate
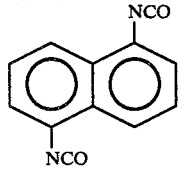

HDI Hexamethylene diisocyanate
NCO—(CH₂)₆—NCO

PAPI Polymethylene polyphenyl isocyanate where p is 0 to 5

-continued

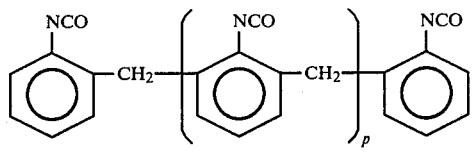

Dicyclohexyl methane 4,4′ diisocyanate

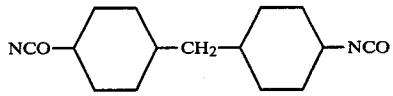

Triphenyl methane triisocyanate

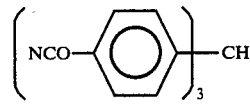

For reasons of biocompatibility, it is preferred to produce polyurethanes in which the group I is the group of phosphatidylcholine itself since such polymers will mimic most closely the outer surface of the lipid matrix of naturally-occurring biological membranes in the body. Thus, it is preferred to work with compounds in which, in the group I, n is 1, m is 2 and R is methyl. However, the use of synthetic analogues of the naturally-occurring phosphatidylcholine structure is also included within the scope of the present invention.

It is usually convenient to use, as one essential reactant, an aliphatic alcohol containing at least three aliphatic hydroxyl groups wherein at least two of those hydroxyl groups are present in free hydroxyl form and at least one of the hydroxyl groups is esterified with a group of formula I as a phosphatidylcholine or homologous ester. Suitable polyols for partial esterification in this way include glycerol, and trimethylolpropane. An example of such a suitable polyol is:

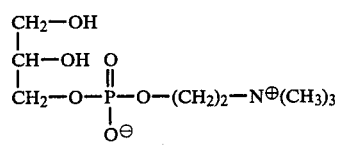

It is not necessary that the functionality of the polyol component be restricted to the free hydroxyl groups and the phosphorus ester group since this component can additionally contain carboxylic ester groups or ether groups. Reactants containing carboxylic ester groups are obtainable for example by reacting polyols such as glycerol, trimethylolpropane or carbohydrates such as hexose, sugars with polyfunctional carboxylic acids (such as adipic acid, sebacic acid, terephthalic acid, phthalic acid etc). Polyether polyols for use in the production of the polymers of the invention can be any of the polyether polyols, e.g. polyethylene glycol, polypropylene glycol etc., that are conventionally used in the production of polyurethanes but which have been modified by partial esterification as the phosphorus ester introducing group I, provided that there are still at least two available hydroxyl groups in the molecule.

It will therefore be seen that while the polyol component used in the invention will normally be a saturated aliphatic compound, it need not necessarily be saturated since it can include carbon-to-carbon unsaturation within the molecule, for example in a unsaturated polyester polyol derived from an unsaturated polycarboxylic acid, or the polyol component can contain cyclic groups as in the case of poly(hydroxymethyl)aromatic reagents.

The reaction between the polyol component of the type described above with the isocyanate will give rise to a polyurethane containing the desired side-chains of formula I. However, if the polyol components of the type described above are the only polyol components used during polyurethane formation, the resulting polyurethane will contain a relatively high proportion of groups I. As a practical matter, we have found that it is desirable for many applications to produce polyurethanes containing less than the maximum possible amount of groups I. It is possible to reduce the proportion of groups I in the polyurethanes by copolymerising the isocyanate component with a polyol component of the type described above and with a further polyol component which does not contain the group I. This further polyol component can simply be an analogue of the first polyol component but which is devoid of the group I. In this situation, the second polyol component will contain at least three reactive hydroxyl groups per molecule e.g. glycerol or trimethylolpropane and will therefore normally introduce crosslinking into the polyurethane structure. As an alternative to or in addition to the use of polyol components containing at least three reactive hydroxyl groups, it is also possible to copolymerise a diol component. The use of a diol component in this way has the effect of extending the polyurethane chain length without introducing crosslinking and without introducing additional groups I and for this reason, this procedure represents a convenient method of modifying the properties of the polyurethane end product and is a preferred procedure.

When a diol component is to be used in the copolymerisation in addition to the hydroxyl reactant introducing the group I and instead of or in addition to polyfunctional hydroxyl components, the diol can be, for example, ethylene glycol, propylene glycol, 1,2-propylene glycol, 1,4-butanediol, 1,3-butanediol, 1,5-pentanediol, diethylene glycol, trimethylene glycol, α,ω-polyoxyethylene diols etc.

The isocyanate component used in the present invention can be any of the isocyanate components conventionally used in the production of polyurethanes. This will often be an aromatic compound having at least two isocyanate groups directly bonded to the aromatic ring system and can be, for example, tolylene diisocyanate, diphenylmethane diisocyanate, naphthalene 1,5-diisocyanate, polymethylenepolyphenyl isocyanate, dicyclohexylmethane 4,4'-diisocyanate, triphenylmethane triisocyanate etc., but it is also possible to use aliphatic diisocyanates, particularly materials such as tetramethylene diisocyanate or hexamethylene diisocyanate. It is not essential that the isocyanate component be a diisocyanate and, in situations where it is desired to introduce crosslinking into the final polyurethane, particularly crosslinking involving aromatic groupings, the isocyanate reactant may be one containing three or more isocyanate groups. At the moment, our preferred isocyanate component is tolylene diisocyanate (TDI) and our preferred hydroxyl component is glycerol monophosphatidylcholine ester (GPC). GPC can be used alone but, for reasons explained above, we prefer to use this in combination with a further polyol component such as glycerol, ethylene glycol or propanediol.

While it is not essential to do so, it is usually convenient to use a material such as GPC in complexed form, usually as a cadmium chloride complex because it is normally isolated from naturally-occurring lipid sources in the form of the cadmium chloride complex. GPC can also be used in the form of a complex with other chlorides of metals of Group IIb of the Periodic Table, e.g., Zn or Hg. It is, of course possible to use this type of hydroxyl component in totally synthetic form but it will normally always be isolated during synthesis in the form of a complex and conveniently used in the complexed form in the polyurethane-forming reaction. When GPC or equivalent reactant is used in uncomplexed form, it can be dissolved in the additional polyol component, when thus used, so avoiding the need for a separate solvent in the polymerisation.

The isocyanate component and the hydroxyl component are reacted together to form the polyurethane under reaction conditions well-known in polyurethane production. A wide variety of reactant ratios can be utilised. If a high molecular weight polyurethane is required, then equivalent proportions of the hydroxyl component and isocyanate component should be used to ensure that essentially all the available hydroxyl and isocyanate groups react with one another to form linear and/or crosslinked polyurethanes. If solid elastomers are required, then a slight excess of the isocyanate component will usually be used to ensure that an isocyanate-terminated prepolymer can be produced and then cured to a final polyurethane. If a thermoplastic material is required, so as to control the melting point of the end polymer, it is necessary to use a hydroxyl component that does not contain the group I in addition to the hydroxyl component containing group I, the ratio between these two hydroxyl components and the molecular weight of the hydroxyl component that does not have the group I being found to influence the thermoplastic character of the final polyurethane. It is also found that control of the relative proportions of hydroxyl component containing the group I to the hydroxyl component not containing the group I is important in controlling the hydrophobic-hydrophilic balance of the final polyurethane.

The polyurethanes of the present invention can be prepared, as mentioned above, by any of the conventional polyurethane production procedures from the isocyanate and hydroxyl component. This reaction can be carried out in a solvent, under solventless conditions or in a two-phase reaction system.

In the solventless system, the isocyanate is run into the hydroxyl component while the temperature is raised, keeping the reaction mixture under vigorous stirring until the melt is homogeneous and the viscosity is high enough. The final step to get a solid elastomer, for instance, is to cure the isocyanate-terminated polymer with a curing agent, e.g. water or a polyol, and heat it. If an unsaturated prepolymer is to be cured, then a peroxide catalyst will be introduced and the mixture heated. The reaction temperature will be chosen according to the melting point and thermostability of the reactants and usually is between 100° and 200° C.

Polyurethane formation in homogeneous solution is usually carried out at room temperature in an appropriate solvent but where the reaction is to be carried out using GPC, which is soluble only in very few solvents, e.g. water and dimethylsulphoxide (DMSO), it is desirable to use a two-phase system where the hydroxyl component is dissolved in an aqueous phase and this is left to react at room temperature with an organic phase containing the diisocyanate.

The use of catalysts in polyurethane formation is well established and catalysts such as sodium acetate, sodium hydroxide, ferric acetylacetonate, tertiary amines such as triethylamine, N,N-dimethylcetylamine, N-substituted morpholines and triethylenediamine as well as organo-metallic compounds such as dibutyl-tin dilaurate and stannous octanoate can be used. The catalyst will be chosen on a polymer-by-polymer basis by reasons of solubility, volatility, lack of odour and influence on reaction rate etc. Reaction inhibitors or reaction modulators such as hydrogen chloride, boric acid, inorganic acids and acid chlorides can also be used in accordance with known procedures.

The polymers of the present invention can be used as construction material for implants or prostheses for the human or animal body, particularly where these implants or prostheses are to come into direct physical contact with blood and where biocompatibility particularly haemocompatibility are required e.g. in heart valves where toughness or flexibility is also required, or as cement in contact lenses. They can also be used in the construction of membranes and other devices that are to be brought into contact with blood or other body fluids on an extra-corpereal basis, for example in heart-lung machines or artificial kidneys. In addition, the polymers of the present invention can be used to coat implants, prostheses, membranes, catheters, contact lenses and other devices which are constructed of another less biocompatible material but which are coated with a polymer according to the present invention to impart biocompatibility to the article. These polymers may also be used in situations where biocompatibility to cell attachment and growth is required such as in tissue culture dishes and substrates. Furthermore, polymers of this type may be used where wettability characteristics e.g. with sea water may be necessary.

The production of prostheses from the polymeric materials we have invented is accomplished generally via the procedures already practised by the polymer industry. When a thermoplastic polymer is obtained it can be processed as a moulding material, e.g. by injection-moulding or extrusion. If a solid elastomer is obtained it can be used in the same processing employed with conventional rubber. The methods required for the processing of polyurethane rubber vary according to the viscosity and reactivity of the intermediate alkyd-isocyanate. Anhydrous conditions are required for the initial chain-lengthening reaction. In many cases there can be also a limited time between compounding the elastomer and shaping and curing.

Isocyanate-terminated adducts are usually processed by melting the alkyd which is then heated under vacuum for about 3 hours at 130° C. to remove water. The diisocyanate is then added and stirred until a homogeneous melt is obtained, at this point a small amount of inhibitor is also added to control the rate of reaction. The cross-linking agent is added next and the melt is then cast into moulds which are maintained at about 110° C. for several hours. Where the polymer of the present invention is to be used for coating, it will be dissolved in a suitable volatile solvent, for example a solvent that has been previously used in the production of the polyurethane, coated onto the article and the solvent allowed to evaporate.

The following Examples are given to illustrate the present invention.

EXAMPLE 1

Polymerisation of glycerophosphatidylcholine Cadmium chloride complex (GPC.Cl$_2$Cd) with tolylene diisocyanate (TDI)

0.79 gr. TDI

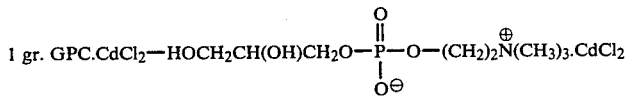

0.1 gr. Tin octanoate
25 ml. Dimethyl sulphoxide (DMSO)

To a stirred solution of 1 gr. of GPC.CdCl$_2$ complex and 0.1 gr. of tin octanoate in 25 ml DMSO were added 0.79 gr of TDI as a mixture of 80% 2,4 and 2,6 isomers. The reaction mixture was stirred overnight at 20° C. and water was added to coagulate the polymer which was then washed with portions each of water, methanol and petroleum ether. The polymer obtained as a white powder shows IR and NMR spectra closely related to GPC plus some new bands assigned to aromatic residues. The polymer is insoluble in a wide range of solvents such as acetone, benzene, chloroform, methanol and tetrahydrofuran (THF).

EXAMPLE 2

Polymerisation of GPC.CdCl$_2$ complex with ethylene glycol and tolylene diisocyanate 0.79 gr. TDI
1 gr GPC.CdCl$_2$
0.14 gr. ethylene glycol
0.1 gr. tin octanoate
25 ml. (DMSO)

The procedure used in Example 1 was followed but a solution containing 1 gr. of GPC.CdCl$_2$, 0.14 gr. ethylene glycol and 0.1 gr. tin octanoate was prepared and 0.79 gr. of TDI were added. The reaction was left to proceed overnight at 20° C. under stirring. A clear yellow solution was obtained and an excess of water was added. The white solid was water and methanol washed and isolated by filtration.

Another formulation with the same components was assayed.
10 gr. TDI
1 gr. GPC.CdCl$_2$
3.1 gr. ethylene glycol
25 ml. DMSO The reaction was carried out without catalyst and a white rigid foam was obtained. The foam was ground and water and methanol washed.

EXAMPLE 3

Polymerisation of GPC.CdCl$_2$ complex with 1,2-propanediol and tolylene diisocyanate 0.79 gr. TDI
1 gr.GPC.CdCl$_2$ 0.17 gr. 1,2-propanediol
0.1 gr. tin octanoate
25 ml. DMSO The reaction mixture prepared following that formulation was stirred overnight at 20° C. A clear yellow solution resulted and an excess of water was added to precipitate the polymer that was water and methanol washed to obtain a clear-brown and hard solid.

EXAMPLE 4

Polymerisation of GPC.CdCl$_2$ complex with glycerol and tolylene diisocyanate 0.98 gr. TDI
1 gr. GPC.CdCl$_2$
0.2 gr. glycerol
0.1 gr. tin octanoate
25 ml. DMSO Applying the same procedure as is described for this series of polymers a white, hard polymer was obtained. Another formulation increasing the proportion of glycerol was assayed as follows.

2.0 gr. TDI
1 gr. GPC.CdCl$_2$
0.5 gr. glycerol
0.1 gr. tin octanoate
25 ml. DMSO The mixture of reactants lead to a very hard foam that was ground and water and methanol washed.

EXAMPLE 5

Polymerisation of GPC.CdCl$_2$ complex with hexamethylenediisocyanate (HDI)

0.76 gr. HDI
1 gr. GPC.CdCl$_2$
0.1 gr. tin octanoate
25 ml. DMSO

A reaction mixture of 1 gr. GPC.CdCl$_2$, 0.1 gr. tin octanoate and 0.76 gr. HDI in 25 ml. DMSO was prepared and continuously stirred overnight at 20° C. A large excess of water was added and a milky solution resulted, after filtration, washing and drying a white solid was obtained. The new material is thermoplastic when heated below 100° C. As a result different shapes can be prepared heating under pressure this new polymer. The polymer swells when exposed to water. The waxy surfaces that can be obtained are clearly hydrophilic when tested for contact angle with water solutions.

EXAMPLE 6

Polymerisation of GPC.CdCl$_2$ complex with ethylene glycol and hexamethylene diisocyanate (HDI)

0.76 gr. HDI
1 gr. GPC.CdCl$_2$
0.14 gr. ethylene glycol
0.1 gr. tin octanoate
25 ml. DMSO The polymer obtained by this solution polymerisation swells in water, however when it is dried it looks like a brittle bulk solid that behaves as a thermoplastic material.

We claim:

1. A polyurethane reaction product of a di- or polyisocyanate and a diol or polyol having at least two hydroxyl groups capable of reacting with an isocyanate group and having the residue of at least one further hydroxyl group present in the form of a phosphorus acid ester group of formula I:

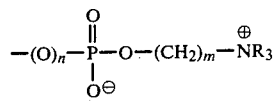

wherein n is 0 or 1, m is 2, 3 or 4 and each R independently is an alkyl group of 1 to 4 carbons.

2. A polyurethane as claimed in claim 1 in which the diol or polyol is glycerol or trimethylolpropane in which one of the hydroxyl groups is esterified with a group of formula I.

3. A polyurethane as claimed in claim 1 in which the group of formula I is

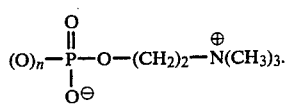

4. A polyurethane as claimed in claim 1 in which the di- or polyisocyanate is tolylene diisocyanate, diphenylmethane diisocyanate, naphthalene 1,5-diisocyanate, polymethylenepolyphenyl isocyanate, dicyclohexylmethane-4,4'-diisocyanate, triphenylmethane triisocyanate, tetramethylene diisocyanate or hexamethylene diisocyanate.

5. A polyurethane as claimed in claim 1 which is the reaction product of a di- or polyisocyanate and a diol or polyol containing a group of formula (I) and a further diol or polyol which does not contain a group of the formula I.

6. A polyurethane as claimed in claim 5 in which the further diol or polyol is glycerol, trimethylolpropane, ethylene glycol, propylene glycol, 1,2-propylene glycol, 1,4-butanediol, 1,3-butanediol, 1,5-pentanediol, diethylene glycol, trimethylene glycol or a α,ω-polyoxyethylene diol.

7. A polyurethane as claimed in claim 1 for use in a method of treatment of the human or animal body by surgery or therapy or of diagnosis practised on the human or animal body.

8. A process for producing polyurethane as claimed in claim 1 which comprises reacting a di- or polyisocyanate with a diol or polyol having at least two hydroxyl groups capable of reacting with an isocyanate group and having at least one further hydroxyl group present in the form of a phosphorus acid ester group of formula I, optionally in the presence of a further diol or polyol which does not contain a group of the formula I.

9. A shaped article in which at least one surface comprises a polyurethane as claimed in claim 1.

10. A shaped article as claimed in claim 9 in which at least one surface is coated with the polyurethane.

11. An article as claimed in claim 9 which is biocompatible preferably haemocompatible.

12. An article as claimed in claim 11 suitable for use in contact with human or animal body fluids.

13. An article as claimed in claim 12 which is a prosthesis, implant, catheter or membrane.

14. A method of medical treatment of the human or animal body which comprises use of an article as claimed in claim 9.

15. A process for the production of an article as claimed in claim 9 which comprises casting, injection moulding or extrusion of the polyurethane.

16. A process for rendering a surface of an article biocompatible preferably haemocompatible in which the components used to produce a polyurethane as claimed in claim 1 are dissolved in a suitable solvent, the surface is coated with this solution and the solvent is evaporated.

* * * * *